(12) United States Patent
Cooke et al.

(10) Patent No.: US 6,173,200 B1
(45) Date of Patent: Jan. 9, 2001

(54) METHOD AND APPARATUS FOR LOCATING TRANSEPICONDYLAR LINE IN A JOINT THAT DEFINES TRANSVERSE ACTION FOR A MOTION

(76) Inventors: T. Derek V. Cooke, c/o Dr. Sulajman Al-Habib Medical Centre, P.O. Box 91877, King Fahad Road - Olaya, Rijadh, 11643 (SA); Brian Kelly, c/o Department of Orthopedics, King Faisal Specialist Hospital and Research Center, Riyadh, 11211 (SA); Gerry Saunders, R. R. #1, Sydenham, Ontario (CA), K0H 2T0

(*) Notice: Under 35 U.S.C. 154(b), the term of this patent shall be extended for 0 days.

(21) Appl. No.: 09/053,465

(22) Filed: Apr. 1, 1998

(30) Foreign Application Priority Data

Apr. 4, 1997 (CA) .................................................. 2201800

(51) Int. Cl.[7] ...................................................... A61B 5/00
(52) U.S. Cl. ............................................. 600/425; 606/87
(58) Field of Search .............................. 600/425; 606/62, 606/95, 96, 97, 87, 88

(56) References Cited

U.S. PATENT DOCUMENTS

| 4,474,177 | * | 10/1984 | Whiteside . | |
|---|---|---|---|---|
| 4,703,751 | * | 11/1987 | Pohl . | |
| 5,281,224 | * | 1/1994 | Faccioli et al. . | |
| 5,514,137 | * | 5/1996 | Coutts . | |
| 5,601,563 | * | 2/1997 | Burke et al. . | |
| 5,720,752 | * | 2/1998 | Elliott et al. | 606/88 |
| 6,090,114 | * | 7/2000 | Matsuno et al. | 606/88 |
| 6,106,529 | * | 7/2000 | Techiera | 606/88 |

* cited by examiner

Primary Examiner—Marvin M. Lateef
Assistant Examiner—Shawna J. Shaw
(74) Attorney, Agent, or Firm—Pearne & Gordon LLP

(57) ABSTRACT

A method for determining the transverse axis for flexion of a condylar ended bone comprises the steps of: conducting a computer tomographic (CT) scan from the end of the condyles inwardly, transverse to the transverse axis of the limb (or extremity) with the joint flexion plane facing forwardly. One then selects the CT slice image exhibiting maximum epicondylar width and establishes a line between the epicondyles at the widest extent. A line is then established joining the posterior condylar tangents on the CT image. Measured lines are established from the posterior condylar tangent line at right angles to the said line between said epicondyles; and then the transverse axis of motion as referenced from the transepicondylar line is obtained.

4 Claims, 5 Drawing Sheets

METHOD AND APPARATUS FOR LOCATING TRANSEPICONDYLAR LINE IN A JOINT THAT DEFINES TRANSVERSE ACTION FOR A MOTION

FIELD OF THE INVENTION

The present invention relates to the field of orthopaedics. In particular, the present invention provide a method and apparatus for axial referencing for surgery involving joints with condyles, such as the knuckle (metacarpo and metatarsophalangeal) joints of hands and feet, elbow and knee.

BACKGROUND OF THE INVENTION

A condyle is the rounded projection at the end of a bone, such as the femur. Condyles may be found in pairs and define rotational bearing surfaces for the joint providing movement mostly in one place (sagittal). Each condyle is shaped generally like a partial disk, with a rounded perimeter, and an outwardly projecting bulge known as the 'epicondyle'.

When a surgeon replaces a joint, such as at the knee, the surgeon will generally reference location of the dissected prosthetic and the prosthetic joint around and to -cover the dissected condylar elements. This is done so that the joint will flex sufficiently to provide a functional angle of motion that is some 90° and reproducible. It is known that ideally, the prosthesis placement ought to be referenced to the transverse axis of the joint, but defining this axis in an accurate reproducible way is generally not possible. Moreover, the transverse axis of the joint is not stationary, but will vary with the state of flexion of the joint. At the knee, however, the transverse axis for motion is approximate with a line joining the epicondyles. An objective therefore is to locate the prosthetic joint appropriately about this transepicondylar line (axis). The problem with this approach has been that the epicondyles are somewhat rounded, making it difficult for the surgeon to accurately locate the most prominent outer aspects of each epicondyle with certainty by viewing the dissected joint. Moreover, the outer aspects of the epicondyles are not reliably visible on frontal or lateral radiographs, because the knee cannot be positioned to radiograph the epicondyles in profile due to overlap of condylar bone. Furthermore, the epicondyles are not readily palpable by hand through the skin. The exception for this is the elbow.

The object of the present invention, therefore, is to provide a method and apparatus for reliably and reproducibly locating the most prominent outer aspects of the epicondyles of a bone such as the femur. This permits a surgeon or technician to locate the transepicondylar line (TEL) of the joint, and use this as the reference the transverse axis of motion about which the location of the condylar portion of the joint prosthesis is then located. The resultant implant is thereby more anatomically located, and capable of flexion without excessive strain or stress on any surrounding tissue usually for more than 90°. A collateral benefit of the method of the present invention is that it provides a wealth of preoperative data to an orthopaedic surgeon, who is then given the opportunity to order precisely sized joint prosthetics well in advance of surgery. This permits an institution to maintain a smaller inventory of joint prosthetics, at a fairly low cost.

In a broad aspect, then, the present invention relates to a method for determining the transepicondylar line of a bone exhibiting condyles and therefore locating the transverse axis of rotation comprising the steps of: (a) conducting a computer tomographic (CT) scan from the end of the condyles inwardly, transverse to the anatomical axis of the bone with the bone facing forwardly; (b) selecting the CT slice image exhibiting maximum epicondylar width and establishing a line between the epicondyles at the widest extent; (c) establishing a line joining the posterior tangents of the condyles on said CT image; (d) establishing measured lines from the posterior condylar tangent line at right angles to the said line between said epicondyles.

In another broad aspect, the present invention relates to a device for locating the epicondyles on a bone that has been prepared by the insertion of a intramedullary rod along the anatomical axis thereof comprising: (a) a body bracket for fixation to said intramedullary rod, against the distal end of said bone; (b) a foot plate depending from said body bracket, adjustable to bear against the posterior surface of a condyle, to fix said body bracket in a -known orientation; (c) a measuring arm extending in the direction of said bone from said bracket, adjustable according to imaging data to locate and permit the marking of a said epicondyle.

BRIEF DESCRIPTION OF THE DRAWINGS

In drawings which illustrate the present invention by way of example.

DETAILED DESCRIPTION OF THE DRAWINGS

This invention will be illustrated by reference to the knee joint, but it will be understood that the invention function equally well in regards to other joints where condyles form the major bearing surface for mainly flexion about a central (horizontal) axis.

Figure 1A:
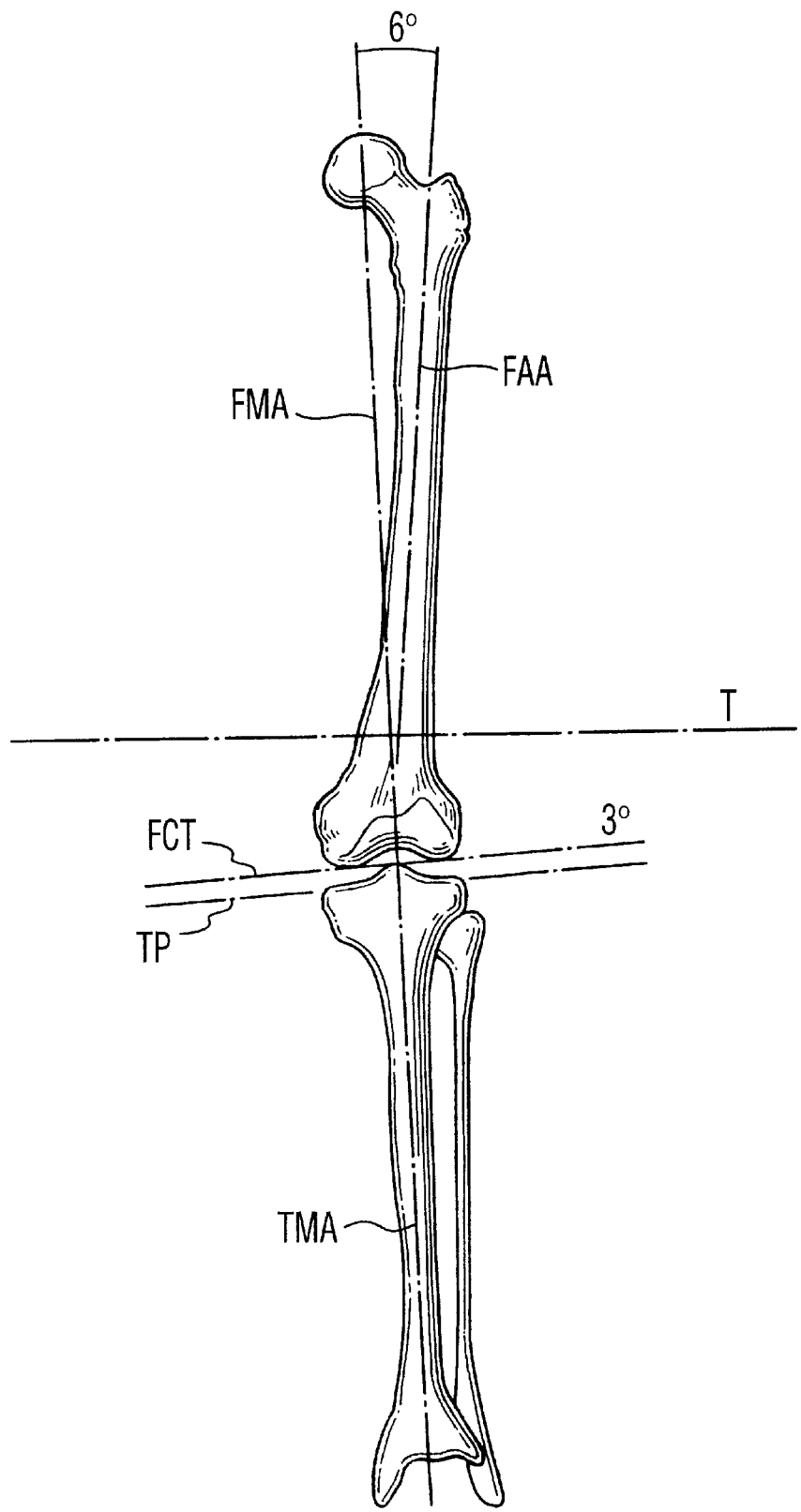
FIG. 1A is a frontal view of a knee joint.

As depicted in FIG. 1A, normal alignment of stance shows the knee. joint line close to horizontal (T) with femoral condylar tangent (FCT) and matching tibial plateaus (TP) inclined three degrees inwardly to a load axis that passes from the foot to the hip on which the knee is centred. In this position the femoral mechanical axis (FMA), being a line joining femoral head to knee centre, is vertical and coincident with the tibial shaft, also its mechanical axis (TMA). In contrast, the femoral shaft anatomic axis (FAA) is angled some 6° to FMA. Referenced from the respective AA the femoral condylar tangent would be 9° valgus more than 90°, whereas tibial plateau would incline 3° varus less than 90° to shaft.

Figure 1B:
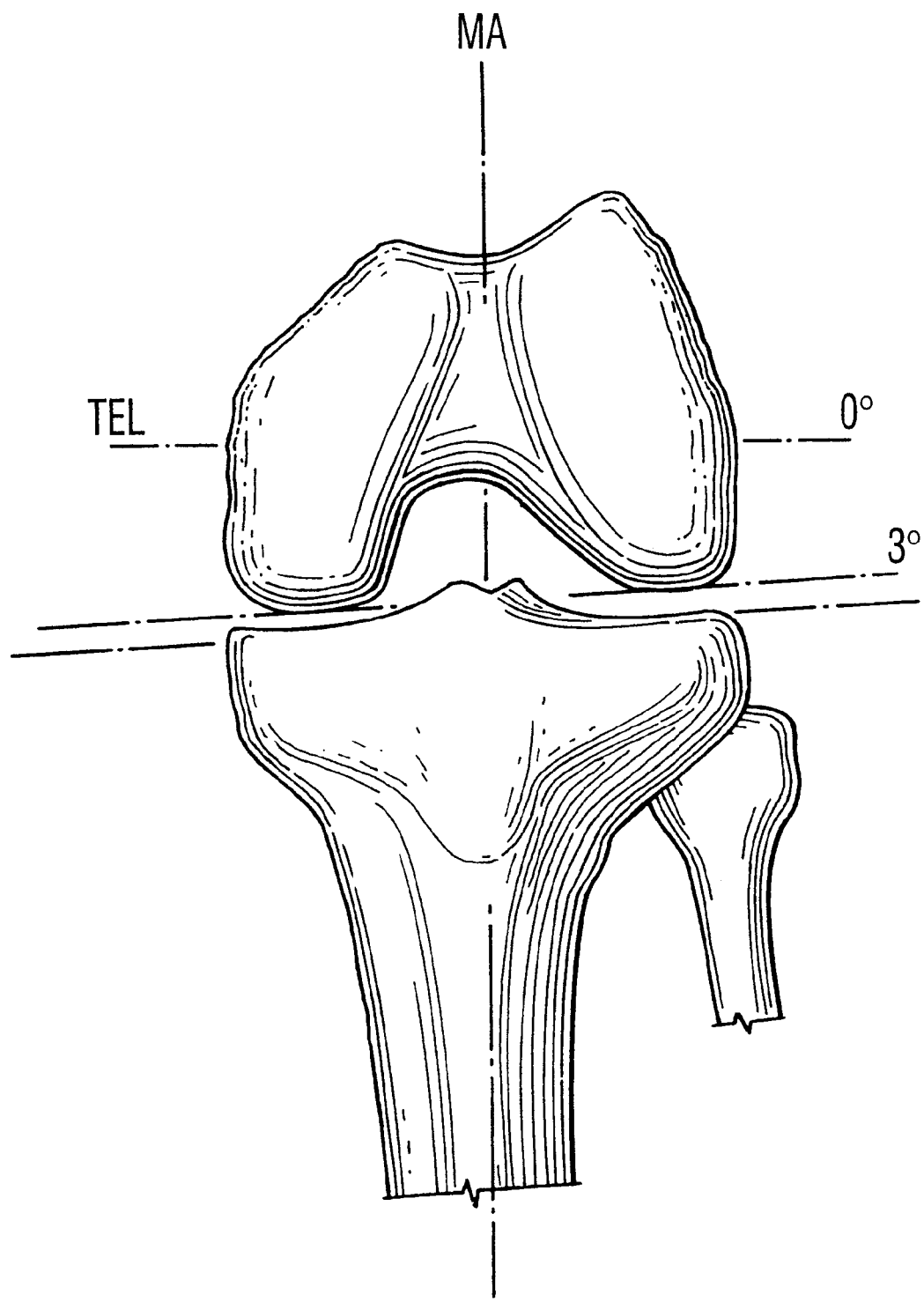
FIG. 1B is an axial view of the distal end of a femur, aligned with a tibia.

FIG. 1B shows an axial orientation of the femur in which the transverse axis is horizontally disposed as line TEL. Note the condylar asymmetry posteriorly reflected by greater posterior prominence medially than laterally. Moreover, neither distal femur or proximal tibia are regularly shaped or parallel to the transverse axis.

Figure 2:
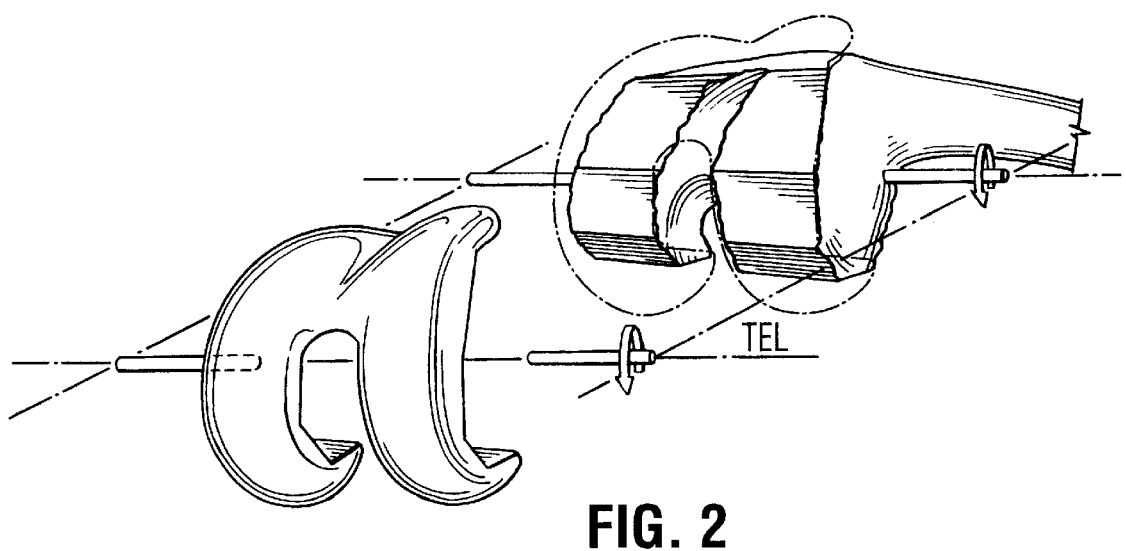
FIG. 2 is a schematic of a knee in flexion, prepared for prosthesis implantation.

FIG. 2 is a schematic of the knee in flexion, prepared for knee implantation in which condylar curve of the implant is located about TEL determined as the transverse axis for rotation.

The TEL is located in the following manner. First, full length frontal standing radiographs of the entire leg, and standing lateral (central on the knee) positioned with flexion plane ahead radiographs are taken. These are used to locate the mechanical and anatomical shaft axis of the femur and tibia.

A CT (computer tomographic) scan of the distal femur is then undertaken, with the subject supine, knee flexion plane ahead, and lower legs parallel with slice separations of, typically 1 mm, through the condylar portion of the femur, including the patella and intracondylar groove.

Figure 3:
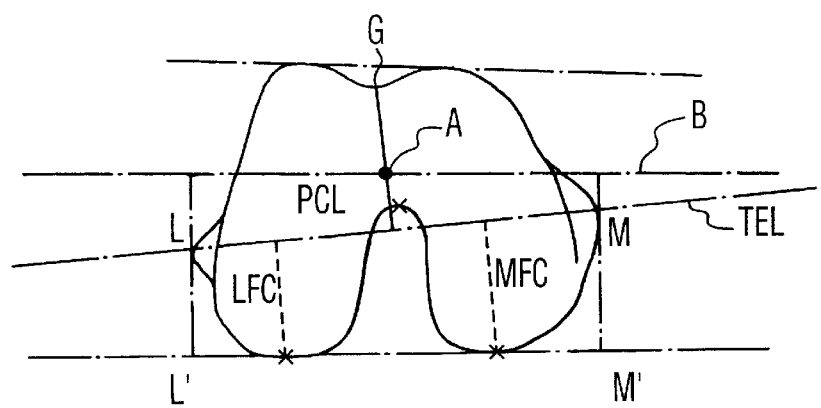
FIG. 3 is a schematic of a CT image through the epicondyles of a femur.
Figure 4:
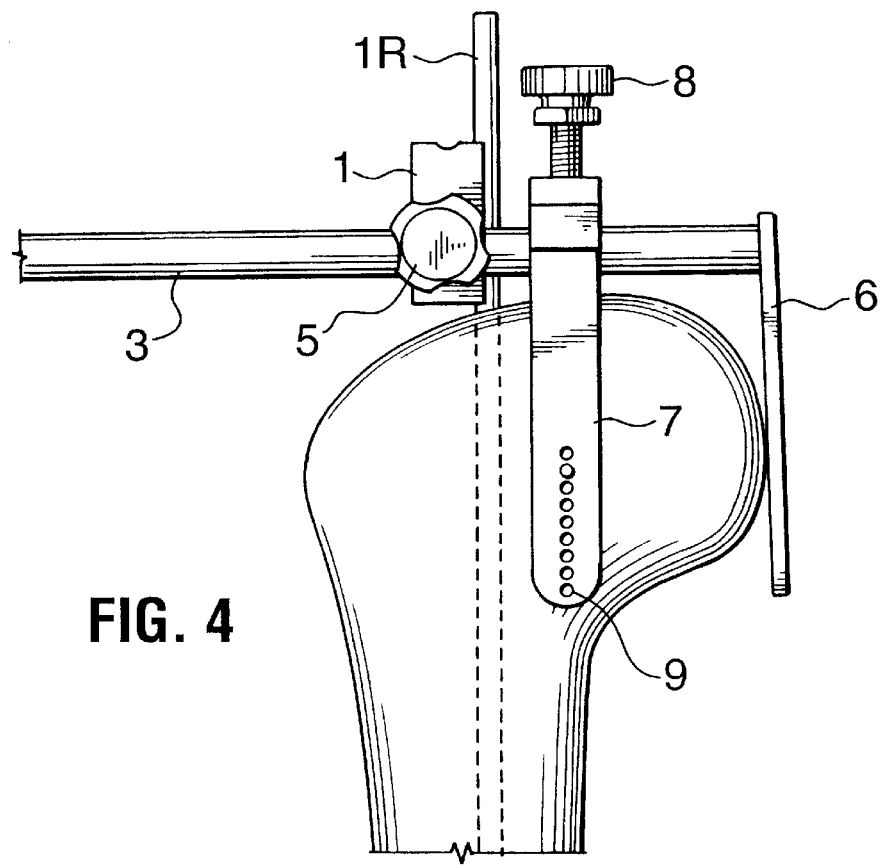
FIG. 4 is a side view of a first embodiment of the apparatus of the present invention attached to a femur.
Figure 5:
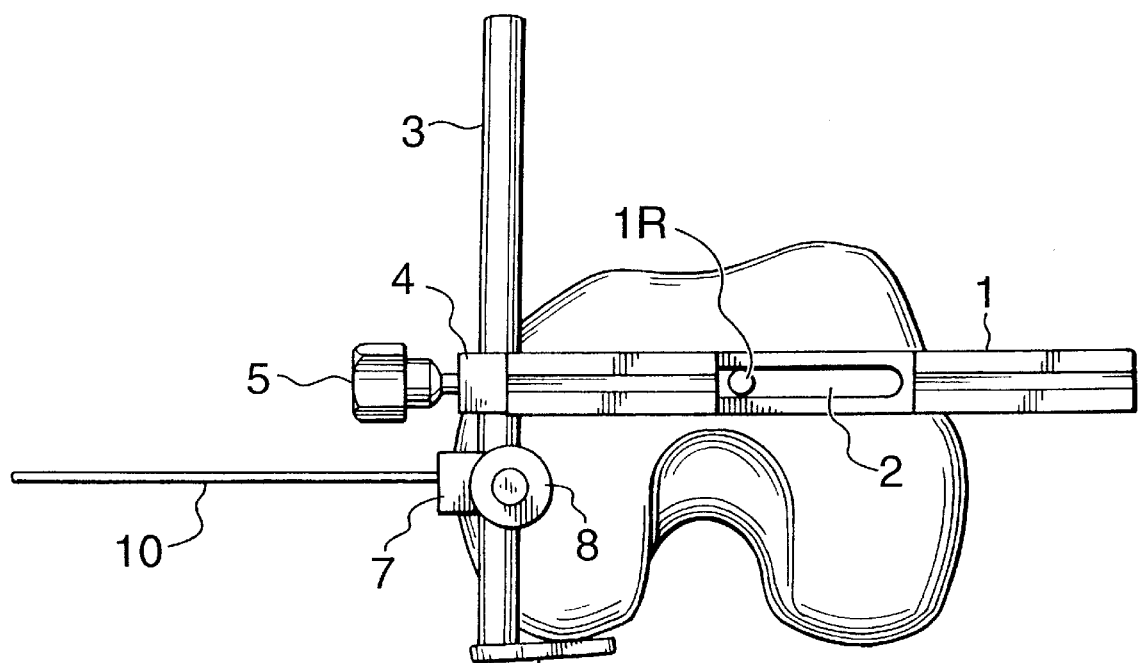
FIG. 5 is a rear view thereof.
Figure 6:
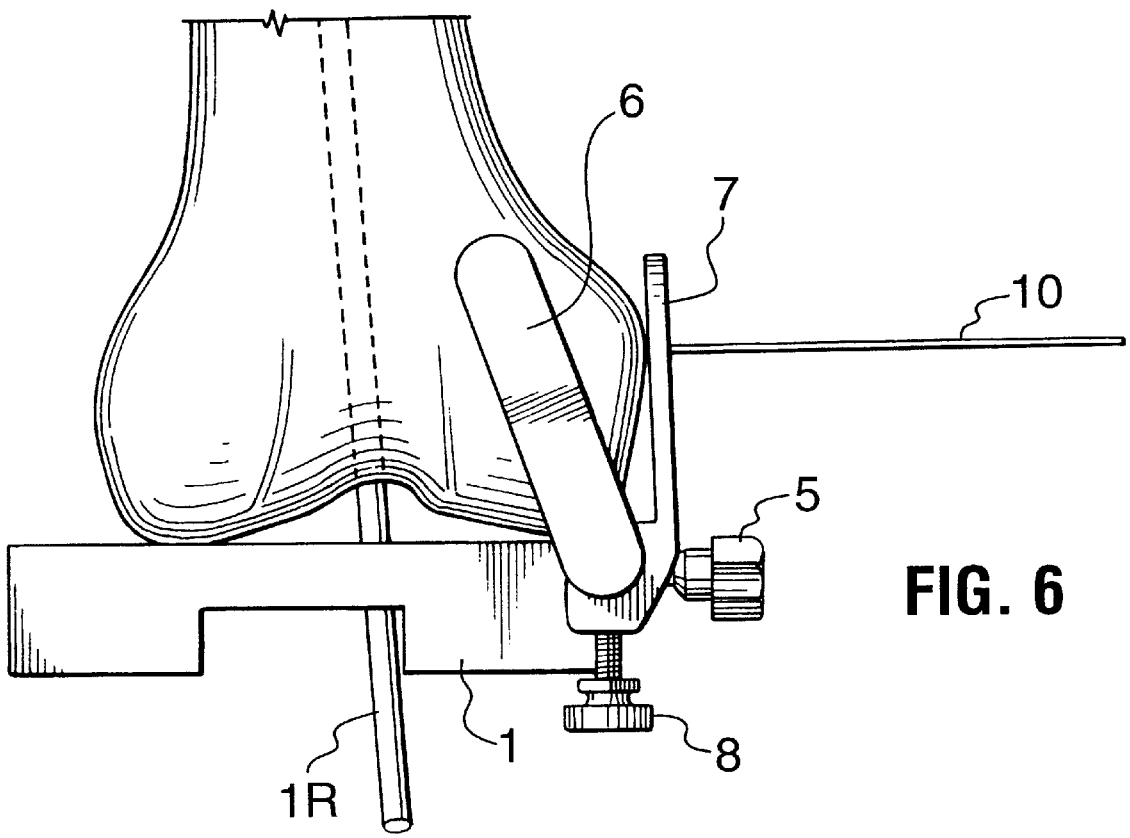
FIG. 6 is an underside view thereof.
Figure 7:
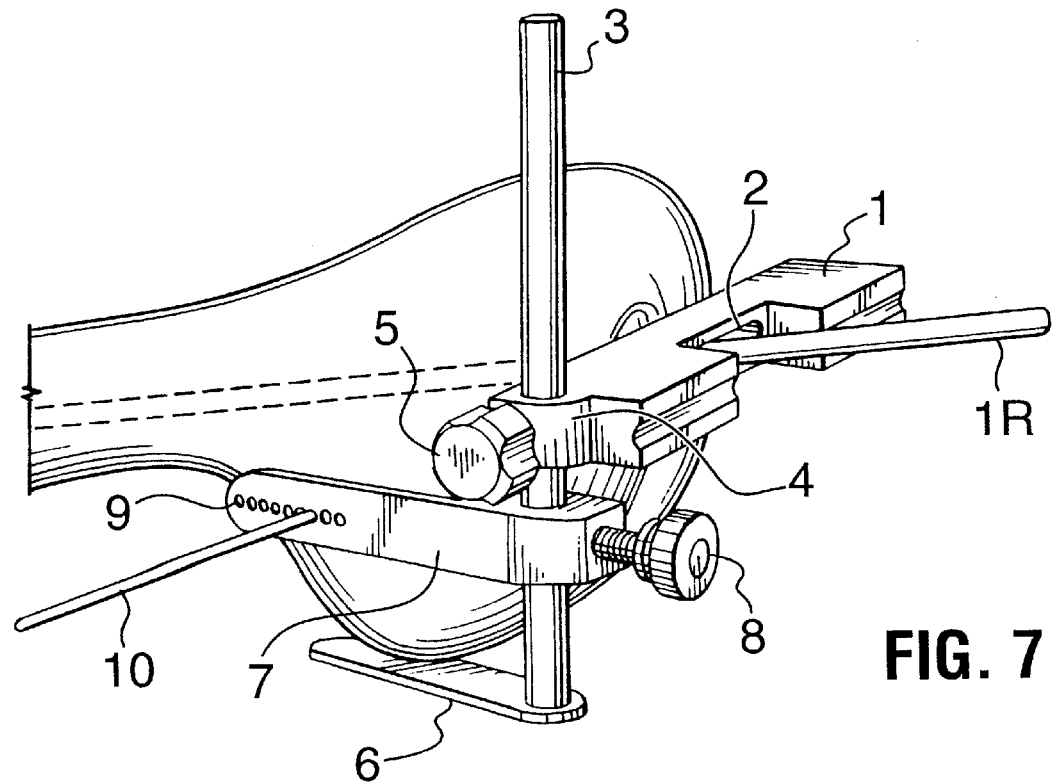
FIG. 7 is a perspective view thereof.

As can be seen in FIG. 3, the outermost aspects of the epicondyles are determinable on a CT slice. The distance of each slice from the distal most aspect of the femur is known. The most outward points of the medial and lateral epicondyle are defined, marked and connected by a line drawn through them. This is the transepicondylar line (TEL) and transverse axis. On the same CT slice, the tangents to the posterior condyles (most posterior projection) are identified and connected by a line. The angle between TEL and the posterior condylar tangent is measured. The centres of each condyle (at the tangent points), centre of the patella groove (G) and centres of each medial and lateral patella flange of the femur as well as the epicondylar tips are identified as points which are connected by lines drawn perpendicular from the TEL to each of them. These interconnections provide the dimensional measures of femoral condylar geometry referenced to the TEL. They are:

TEL-LFC/MFC. Perpendicular distances from TEL to respective condylar tangents—represent condylar depths (and radii);

PCL (Posterior cruciate ligament) point location at TEL—represents the knee mediolateral centre;

PCL distance to medial (MO or lateral (L) epicondyle [condylar width];

TEL-G—Sulcus location and height at TEL.

The condylar depths and radii thus measured, and overall femoral width at the TEL provides the surgeon with precise sizing and locating information.

The long leg radiograph gives information to define femoral geometry in frontal plane. From it the femoral mechanical axis (MA) is drawn and referenced for its variance to the anatomic axis. (Usually about 6°–7°). The lateral radiograph defines any unusual curvature of the bone to the hip.

In the operating room four points are established of distal femoral geometry that will be used to define each medial and lateral epicondyle and subsequently the TEL. These are:

Posterior cruciate ligament attachment at its anterolateral point;

Medial femoral tangent posteriorly;

Lateral femoral tangent posteriorly.

Referring now to FIGS. 4, 5, 6 and 7, the instrument and method of the present invention are illustrated. Preparatory to utilizing the present invention, the distal femur is penetrated above the PCL point at A, and an intramedullary rod is inserted into the shaft of the femur defining the anatomic axis of the femur. The rod is immobilized with a sliding bushing.

The TEL locating device of the present invention is shown in FIGS. 4, 5, 6 and 7. This device is utilized to locate and mark the outermost aspects of the femoral condyles one at a time. It includes a central bracket 1 with a central bored through slot 2 that is dimensioned to permit the bracket to be slid onto and fixed on the intramedullary rod (IR) that has been inserted in the femur, as aforesaid. The slot is wide enough to accommodate a wide range of intracondylar widths, and is marked (not illustrated) to permit accurate placement.

At one end of the bracket a rod 3 is mounted in a sleeve 4 fixed to the end of the bracket. The sleeve is provided with a set screw 5, to fix the rod 3 at any desired height. The rod is marked along its length so as to be easily set for height.

One end of the rod is provided with a foot 6 plat that extends forwardly, to contact the posterior surface of a condyle. A forwardly projecting measuring and positioning arm is mounted on the rod, between the bracket and the foot plate. The measuring arm may be fixed on the rod by means of a thumb screw 8, provided on the end of the measuring element.

In order to utilize the device of FIGS. 4 to 7, measurements taken from the CT scan slice diagram exemplified by FIG. 3 are utilized. The position A of the intramedullary rod through the anatomical axis of the femur, is known. A line B is drawn through that position, parallel to the posterior femoral tangent, and measurements taken from that line to the posterior femoral tangent. This provides the height setting for the rod at the end of the tangent. Epicondylar tangent lines L–L' and M–M' provide the settings, on each side, for the measuring arms. These tangent lines are then extrapolated to intersect the line through the anatomical axis of the femur, providing the setting for the point of fixation of the bracket on the intramedullary rod.

With the foregoing measurements known, the rod is first fixed on the bracket at the desired height. The bracket is then slid onto the intramedullary rod, and adjusted lateromedially to the desired location, as measured in the manner described above, and fixed in position (fixation means not illustrated), with the foot plate in contact with the posterior of a selected condyle (illustrated is the lateral one). The measuring arm is then brought to the desired, premeasured height, and pivoted over into contact with the epicondyle. The thumbscrew on the measuring arm is then tightened. The arm is provided with marked gradations of measurement, corresponding to the position of CT image slices. As illustrated, there may be a series of apertures 9, but other methods of marking gradations may be used. The correct point according to the level of the CT image is chosen, and the epicondyle marked for instance by a pin 10. The process is repeated for the other side of the femur, with the bracket inverted and the rod reinserted. At this time it may be necessary to consult a different CT image slice, if the two epicondyles were not located on the same image.

Utilizing the present invention precisely defines two critical axes from which all further measurements and bone preparative steps are made. These may be checked against CT and plain radiograph data from time to time during surgery. These include:

Anterior patella groove height. G-TEL

Posterior condylar depth TEL-MFC, TEL-LFC

Mean condylar depth mid-point between MFC/LFC

Condylar width at TEL.

It will be understood that the mechanical configuration of the device of the present invention may be easily altered without departing from the present invention. For instance, the foot plates may be constructed to slide medially/laterally, and in this instance, the L-shaped square may be replaced by a calibrated rod. Alternatively, a calibrated protractor centred at the PCL point may be used to define an angle from the transepicondylar axis to the PC tangent. Once set, the protractor arm is moved to a preset location at centre defining the ends of the transepicondylar axis.

The TEL locating information derived from the first part of the method of the present invention may also be used to define the TEL by means of known three dimensional computerized magnetic tracking techniques. With the joint immobilized, the TEL may be precisely located by its position relative to the distal end of the femur, and the posterior tangent of the condyles, both of which may be reliably located in a joint dissection. The angular orientation and distance of the epicondyles relative to these two lines derived by the method of the present invention may be utilized to quickly and efficiently locate the TEL by thee dimensional magnetic tracking.

It is to be understood that the examples described above are not meant to limit the scope of the present invention. It is expected that numerous variants will be obvious to the person skilled in the field of orthopaedic instrument design without any departure from the spirit of the invention. The appended claims, properly construed, form the only limitation upon the scope of the invention.

The embodiments of the invention in which an exclusive property or privilege is claimed are defined as follows:

1. A device for locating the epicondyles on a bone that has been prepared by the insertion of a intramedullary rod along the anatomical axis thereof comprising:

a) a body bracket for fixation to said intramedullary rod, against the distal end of a bone, said bracket having an end and a side, said side being approximately perpendicular to said end;

b) a foot plate depending from said side of said body bracket, adjustable to bear against the posterior of a condyle, to fix said body bracket in a known orientation;

c) a measuring arm extending in the direction of said bone from said end of said bracket, adjustable according to imaging data to locate and permit the marking of an epicondyle.

2. A device as claimed in claim 1, wherein said foot plate is parallel to said bracket, to orient said bracket parallel to the posterior condylar tangent of a bone.

3. A device as claimed in claim 2, wherein said foot plate is located at the end of a rod adjustable in a sleeve at the end of said body bracket.

4. A device as claimed in claim 3, wherein said measuring arm extends forwardly from said foot plate rod, between said bracket and said foot plate, said measuring arm including means for fixing the location thereof on said foot plate rod.

* * * * *

UNITED STATES PATENT AND TRADEMARK OFFICE
CERTIFICATE OF CORRECTION

PATENT NO. : 6,173,200
DATED : January 9, 2001
INVENTOR(S) : Cooke et al.

It is certified that error appears in the above-indentified patent and that said Letters Patent is hereby corrected as shown below:

On the Title Page, Item (76), Line 4, delete "Rijadh" and insert therefore --Riyadh--.

On the Title Page, Item (76), line 6, delete "Center" and insert therefore --Centre--.

Signed and Sealed this

Twenty-ninth Day of May, 2001

Attest:

NICHOLAS P. GODICI

*Attesting Officer*    *Acting Director of the United States Patent and Trademark Office*